United States Patent
Quallich et al.

(10) Patent No.: US 6,388,127 B1
(45) Date of Patent: *May 14, 2002

(54) PROCESS FOR PREPARING CYCLIC THIOAMIDES

(75) Inventors: George Joseph Quallich; Jeffrey William Raggon, both of North Stonington; Paul D. Hill, Groton, all of CT (US)

(73) Assignee: Pfizer INC, New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/536,576

(22) Filed: Mar. 28, 2000

Related U.S. Application Data

(60) Provisional application No. 60/126,831, filed on Mar. 30, 1999.

(51) Int. Cl.$^7$ .................. C07C 315/00; C07D 275/10
(52) U.S. Cl. .................. 562/426; 544/58.2; 544/98; 544/386; 562/426; 562/433; 562/443; 564/218; 564/305
(58) Field of Search .................. 544/58.2, 98, 386; 562/426, 433, 443; 564/218, 305

(56) References Cited

U.S. PATENT DOCUMENTS 2,755,278 A  7/1956  Hoffman-La Roche

FOREIGN PATENT DOCUMENTS

| WO | WO 94/13652 A |   | 3/1994 |
|----|---------------|---|--------|
| WO | WO 94/3652    | * | 6/1994 |
| WO | WO 98/14433 A |   | 4/1998 |

OTHER PUBLICATIONS

Weissman, S et al Tetrahedron Lett (1998) 39(41) 7459–7462.*
Blommaert, A et al, J. Med Chem. (1993 36(20) 2868–77.*
Giannangeli M., et al."Effect of Modifications of the Alkylpiperazine Moiety of Trazodone on 5HT2A and alpha–1 Receptor Binding Affinity," *Journal of Medicinal Chemistry*, vol. 42, No. 3, pp. 336–345, 1999.
Bischoff C.A. et al., "Ueber Diphenyl–monaci–und –diacipiperazin," *Chemische Berichte*, vol. 23, p. 2026, 1890.
Bhat B., et al.: "Possible Antimalarial Agents: Syntheses of 6–Methoxy–8–substituted–aminoquinolines," *Indian Journal of Chemistry*, vol. 24, pp. 419–423, Apr. 1985.
W. Gary Phillips, et al.: "Chemistry of α, α–Dichlorosulfenyl Chlorides," *J. Org. Chem.*, vol. 37, No. 10, pp. 1526–1531, 1972.

* cited by examiner

*Primary Examiner*—Paul J. Killos
(74) *Attorney, Agent, or Firm*—Peter C. Richardson; Paul H. Ginsburg

(57) ABSTRACT

The present invention relates to a process for preparing a compound of the formula

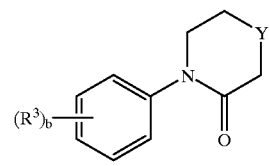

I wherein b, Y and R$^3$ are defined as above, useful for preparing novel aralkyl and aralkylidene heterocyclic lactams and imides which are selective agonists and antagonists of serotonin 1 (5-HT$_1$) receptors.

14 Claims, No Drawings

PROCESS FOR PREPARING CYCLIC THIOAMIDES

This application claims priority under 35 U.S.C. §119(e) from U.S. application Ser. No. 60/126,831, filed Mar. 30, 1999, which application is hereby incorporated by reference.

BACKGROUND OF THE INVENTION

The present invention relates to a process for preparing cyclic thioamides useful for preparing aralkyl and aralkylidene heterocyclic lactams and imides, which are selective agonists and antagonists of serotonin 1 (5-$HT_1$) receptors, specifically, of one or both of the 5-$HT_{1A}$ and 5-$HT_{1D}$ receptors, useful in treating or preventing migraine, depression and other disorders for which a 5-$HT_1$ agonist or antagonist is indicated.

European Patent Publication 434,561, published on Jun. 26, 1991, refers to 7-alkyl, alkoxy, and hydroxy substituted-1-(4-substituted-1-piperazinyl)-naphthalenes. The compounds are referred to as 5-$HT_1$ agonists and antagonists useful for the treatment of migraine, depression, anxiety, schizophrenia, stress and pain.

European Patent Publication 343,050, published on Nov. 23, 1989, refers to 7-unsubstituted, halogenated, and methoxy substituted-1-(4-substituted-1-piperazinyl)-naphthalenes as useful 5-$HT_{1A}$ ligand therapeutics.

PCT publication WO 94/21619, published Sep. 29, 1994, refers to naphthalene derivatives as 5-$HT_1$ agonists and antagonists.

PCT publication WO 96/00720, published Jan. 11, 1996, refers to naphthyl ethers as useful 5-$HT_1$ agonists and antagonists.

European Patent Publication 701,819, published Mar. 20, 1996, refers to the use of 5-$HT_1$ agonists and antagonists in combination with a 5-HT re-uptake inhibitor.

Glennon et al., refers to 7-methoxy-1-(1-piperazinyl)-naphthalene as a useful 5-$HT_1$ ligand in their article "5-$HT_{1D}$ Serotonin Receptors", *Clinical Drug Res. Dev.*, 22, 25–36 (1991).

Glennon's article "Serotonin Receptors: Clinical Implications", *Neuroscience and Behavioral Reviews*, 14, 35–47 (1990), refers to the pharmacological effects associated with serotonin receptors including appetite suppression, thermoregulation, cardiovascular/hypotensive effects, sleep, psychosis, anxiety, depression, nausea, emesis, Alzheimer's disease, Parkinson's disease and Huntington's disease.

World Patent Application WO 95/31988, published Nov. 30, 1995, refers to the use of a 5-$HTD_{1D}$ antagonist in combination with a 5-$HT_{1A}$ antagonist to treat CNS disorders such as depression, generalized anxiety, panic disorder, agoraphobia, social phobias, obsessive-compulsive disorder, post-traumatic stress disorder, memory disorders, anorexia nervosa and bulimia nervosa, Parkinson's disease, tardive dyskinesias, endocrine disorders such as hyperprolactinaemia, vasospasm (particularly in the cerebral vasculature) and hypertension, disorders of the gastrointestinal tract where changes in motility and secretion are involved, as well as sexual dysfunction.

G. Maura et al., *J. Neurochem*, 66 (1), 203–209 (1996), have stated that administration of agonists selective for 5-$HT_{1A}$ receptors or for both 5-$HT_{1A}$ and 5-$HT_{1D}$ receptors might represent a great improvement in the treatment of human cerebellar ataxias, a multifaceted syndrome for which no established therapy is available.

European Patent Publication 666,261, published Aug. 9, 1995 refers to thiazine and thiomorpholine derivatives which are claimed to be useful for the treatment of cataracts.

SUMMARY OF THE INVENTION

The present invention relates to a process for preparing a compound of the formula

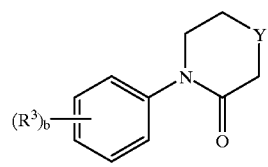

I wherein b is 0, 1, 2 or 3; Y is oxygen, sulfur, NH or N-acetyl; and each $R^3$ is independently selected from the group consisting of halo, cyano, ($C_1$–$C_6$)alkyl, ($C_1$–$C_6$)alkoxy and trifluoromethyl; comprising reacting a compound of the formula

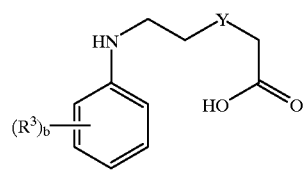

II with a dehydrating agent.

The present invention also relates to a more preferred process for preparing the compound of formula I, wherein the dehydrating agent is acetic anhydride.

The present invention also relates to a process for preparing a compound of the formula

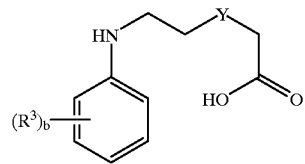

II comprising reacting a compound of the formula

III with haloacetic acid in the presence of a base.

The present invention also relates to a more preferred process for preparing the compound of formula II, wherein the haloacetic acid is bromoacetic acid.

The present invention also relates to a more preferred process for preparing the compound of formula II, wherein the base is potassium hydroxide.

The present invention also relates to a process for preparing a compound of the formula

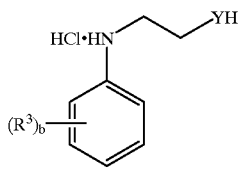

comprising reacting a compound of the formula

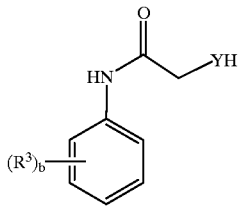

with a reducing agent and reacting the compound so formed with hydrochloric acid.

The present invention also relates to a more preferred process for preparing the compound of formula III, wherein the reducing agent is borane tetrahydrofuran complex.

The present invention also relates to a process for preparing a compound of the formula

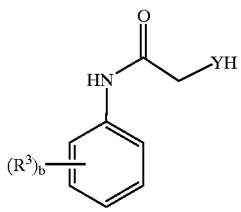

comprising reacting a compound of the formula

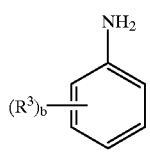

with hydroxyacetic acid, mercaptoacetic acid or 2-aminoacetic acid.

The present invention also relates to a more preferred process for preparing the compound of formula IV, wherein the compound of formula V is reacted with mercaptoacetic acid.

The present invention also relates to a process for preparing a compound of the formula

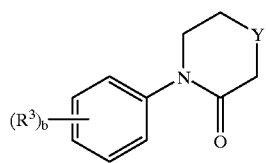

wherein b is 0, 1, 2 or 3; Y is oxygen, sulfur, NH or N-acetyl; and each $R^3$ is independently selected from the group consisting of halo, cyano, $(C_1-C_6)$alkyl, $(C_1-C_6)$alkoxy and trifluoromethyl; comprising (a) reacting a compound of the formula

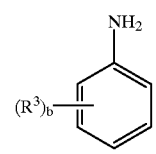

with hydroxyacetic acid, mercaptoacetic acid or 2-aminoacetic acid;

(b) reacting a compound of formula IV so formed

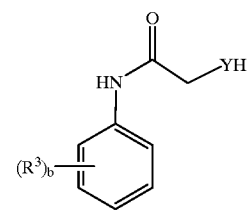

with a reducing agent and reacting the intermediate compound so formed with hydrochloric acid;

(c) reacting a compound of formula III so formed

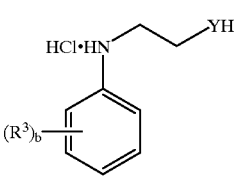

with haloacetic acid in the presence of a base; and (d) reacting a compound of formula II so formed

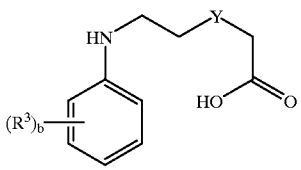

with a dehydrating agent.

The present invention also relates to a more preferred process for preparing the compound of formula I, wherein the compound of formula V is reacted with mercaptoacetic acid; the reducing agent is borane tetrahydrofuran complex;

the base is potassium hydroxide; the haloacetic acid is bromoacetic acid; and the dehydrating agent is acetic anhydride.

The present invention also relates to a compound of the formula

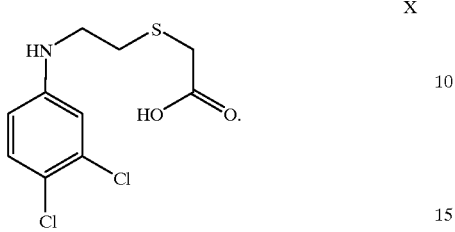

X

The present invention also relates to a compound of the formula

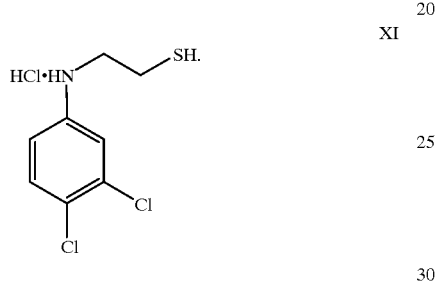

XI

The present invention also relates to a compound of the formula

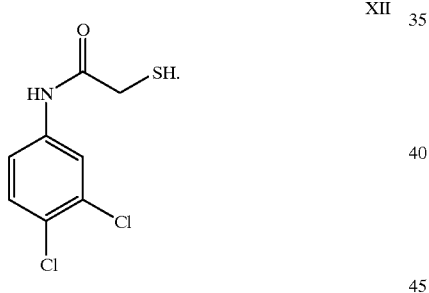

XII

DETAILED DESCRIPTION OF THE INVENTION

The following reaction Schemes illustrate the preparation of the compounds of the present invention. Unless otherwise indicated, b, Y and $R^3$ in the reaction Schemes and the discussion that follow are defined as above.

SCHEME 1

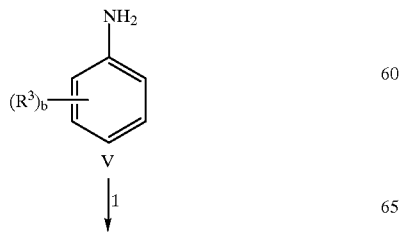

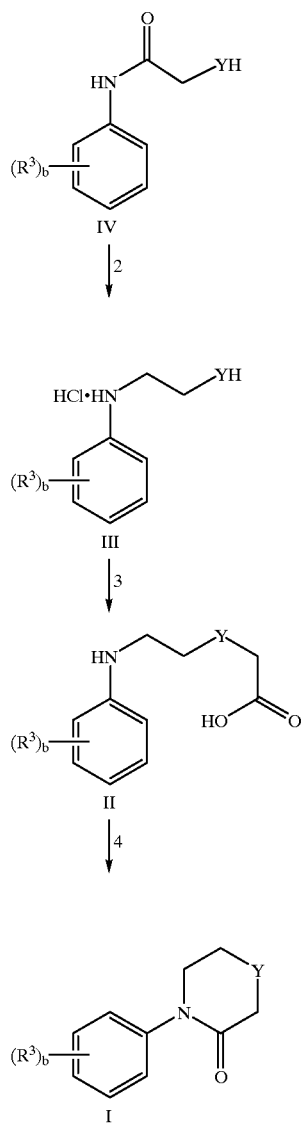

SCHEME 2

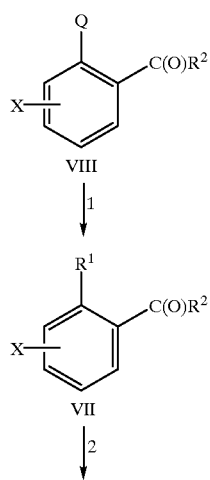

-continued

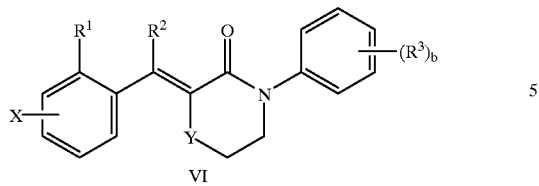

In reaction 1 of Scheme 1, the aniline compound of formula V is converted to the corresponding compound of formula IV, wherein Y is oxygen, sulfur, NH or N-acetyl, by reacting V with hydroxyacetic acid, mercaptoacetic acid or 2-aminoacetic acid, in the presence of an aprotic solvent, such as toluene. The reaction mixture so formed is heated to reflux for a time period between 16 hours to about 24 hours, preferably about 20 hours.

In reaction 2 of Scheme 1, the compound of formula IV is converted to the corresponding compound of formula III by reducing IV with a reducing agent, such as borane tetrahydrofuran complex. The compound so formed is then treated with anhydrous hydrochloric acid in the presence of a polar protic solvent, such as ethanol. The reaction is carried out at a temperature between about 10° C. to about 20° C., preferably about 15° C., for a time period between about 2 hours to about 4 hours, preferably about 3 hours.

In reaction 3 of Scheme 1, the compound of formula III is converted to the corresponding compound of formula II by first treating III with a base, such as potassium hydroxide, under inert atmosphere, in the presence of a polar protic solvent, such as ethanol, at a temperature between about 0°C. to about 20° C., preferably about 10° C., for a time period between about 0.5 hours to about 2 hours, preferably about 1 hour. Alkylation of the intermediate compound so formed is carried out with the addition of bromoacetic acid. The reaction mixture is then stirred for an additional time period between about 2 hours to about 4 hours, preferably about 3 hours.

In reaction 4 of Scheme 1, the compound of formula II is converted to the corresponding compound of formula I by reacting II with excess acetic anhydride. The reaction mixture so formed is heated to reflux for a time period between about 0.5 hours to about 2 hours, preferably about 1 hour.

In reaction 1 of Scheme 2, the compound of formula VIII, wherein Q is a suitable leaving group, such as halo, preferably fluoro; X is hydrogen, chloro, fluoro, bromo, iodo, cyano, $(C_1-C_6)$alkyl, hydroxy, trifluoromethyl, $(C_1-C_6)$alkoxy, —$SO_t(C_1-C_6)$alkyl wherein t is zero, one or two, —$CO_2R^8$ or —$CONR^9R^{10}$; wherein $R^8$, $R^9$ and $R^{10}$ are each independently selected from hydrogen, $(C_1-C_4)$alkyl, phenyl or naphthyl, wherein said phenyl or naphthyl may optionally be substituted with one or more substituents independently selected from chloro, fluoro, bromo, iodo, $(C_1-C_6)$alkyl, $(C_1-C_6)$alkoxy, trifluoromethyl, cyano and —$SO_k(C_1-C_6)$alkyl wherein k is zero, one or two; and $R^2$ is hydrogen, $(C_1-C_4)$alkyl, phenyl or naphthyl, wherein said phenyl or naphthyl may optionally be substituted with one or more substituents independently selected from chloro, fluoro, bromo, iodo, $(C_1-C_6)$alkyl, $(C_1-C_6)$alkoxy, trifluoromethyl, cyano and —$SO_k(C_1-C_6)$alkyl wherein k is zero, one or two; is converted to the corresponding compound of formula VII, wherein $R^1$ is a group of the formula $G^1$, $G^2$, $G^3$, $G^4$, $G^5$ or $G^6$ depicted below,

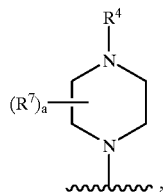
$G^1$

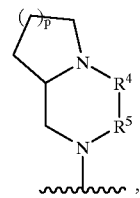
$G^2$

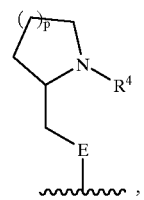
$G^3$

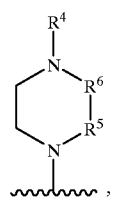
$G^4$

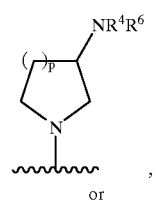
$G^5$ or

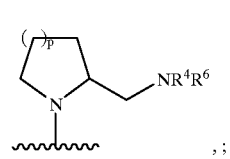
$G^6$ a is zero to four; p is 1, 2 or 3; $R^4$ is selected from the group consisting of hydrogen, $(C_1-C_6)$alkyl optionally substituted with $(C_1-C_6)$alkoxy or one to three fluorine atoms, or $[(C_1-C_4)$alkyl]aryl wherein the aryl moiety is phenyl, naphthyl, or heteroaryl-$(CH_2)_q$—, wherein the heteroaryl moiety is selected from the group consisting of pyridyl, pyrimidyl, benzoxazolyl, benzothiazolyl, benzisoxazolyl and benzisothiazolyl and q is zero, one, two, three or four, and wherein said aryl and heteroaryl moieties may optionally be substituted with one or more substituents independently selected from the group consisting of chloro, fluoro, bromo, iodo, $(C_1-C_6)$alkyl, $(C_1-C_6)$alkoxy, trifluoromethyl, cyano and —$SO_g(C_1-C_6)$alkyl, wherein g is zero, one or two; $R^5$ is selected from the group consisting of hydrogen, ($C_1$–$C_6$)alkyl, [($C_1$–$C_4$)alkyl]aryl wherein the aryl moiety is phenyl, naphthyl, or heteroaryl-$(CH_2)_r$—, wherein the heteroaryl moiety is selected from the group consisting of pyridyl, pyrimidyl, benzoxazolyl, benzothiazolyl, benzisoxazolyl and benzisothiazolyl and r is zero, one, two, three or four, and wherein said aryl and heteroaryl moieties may optionally be substituted with one or more substituents independently selected from the group consisting of chloro, fluoro, bromo, iodo, ($C_1$–$C_6$)alkyl, ($C_1$–$C_6$)alkoxy, trifluoromethyl, —C(=O)—($C_1$–$C_6$)alkyl, cyano and —$SO_j$($C_1$–$C_6$)alkyl, wherein j is zero, one or two; or $R^4$ and $R^5$ taken together form a 2 to 4 carbon chain; $R^6$ is hydrogen or ($C_1$–$C_6$)alkyl; each $R^7$ is, independently, ($C_1$–$C_4$)alkyl or a ($C_1$–$C_4$)methylene bridge from one of the ring carbons of the piperazine ring of $G^1$ to the same or another ring carbon or a ring nitrogen of the piperazine ring of $G^1$ having an available bonding site, or to a carbon of $R^4$ having an available bonding site; and E, of formula $G^3$, is oxygen, sulfur, SO or $SO_2$; by reacting VIII with a compound of formula $R^1H$, wherein H refers to a hydrogen atom on group E from $G^3$ or nitrogen atoms from $G^1$, $G^2$, $G^4$, $G^5$ or $G^6$ and $R^1$ is defined as above, in the presence of base. This reaction is generally carried out at a temperature from about 25° C. to about 140° C., preferably at about the reflux temperature, in a polar aprotic solvent, such as dimethyl sulfoxide, N,N-dimethylformamide, N,N-dimethylacetamide or N-methyl-2-pyrrolidinone, preferably N-methyl-2-pyrrolidinone. Suitable bases include anhydrous sodium carbonate, potassium carbonate, sodium hydroxide and potassium hydroxide, as well as amines such as pyrrolidine, triethylamine and pyridine. Anhydrous potassium carbonate is preferred.

In reaction 2 of Scheme 2, the compound of formula VII is converted to the corresponding compound of formula VI by subjecting VII to an Aldol condensation-elimination. In an Aldol condensation, the compound of the formula VII is reacted with a compound of the formula I

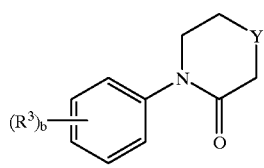

I in the presence of a base, to form an Aldol intermediate of the formula IX

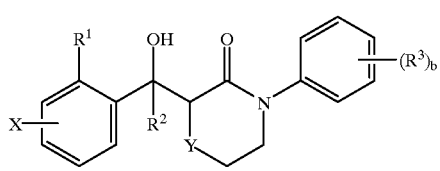

IX which may be isolated or, preferably, converted directly in the same reaction step to a compound of formula VI by the loss of water. The degree of completion for the conversion of compound of formula IX to the aldol product of formula VI may be assessed using one or more analytical techniques, such as thin layer chromatography (tlc) or high pressure liquid chromatography (hplc). In some instances it may be possible or desirable to isolate the intermediate of formula IX. In such case, the compound of formula IX may be converted into the compound of formula VI by the elimination of water using techniques which are familiar to those skilled in the art, for example, by heating to the reflux temperature a solution of the compound of formula IX in a solvent such as benzene, toluene or xylene, in the presence of a catalytic amount of benzene- or p-toluene-sulfonic acid with provision for the removal of the water generated. Such water removal techniques may involve the use of molecular sieves or a Dean-Stark trap to isolate the water created as an azeotrope with the solvent.

The Aldol reaction is typically carried out in an ether solvent such as methyl t-butyl ether, isopropyl ether or tetrahydrofuran, at a temperature from about −78° C. to about 25° C. Preferably, this reaction is carried out in tetrahydrofuran at about 25° C. Suitable bases for use in the aldol formation step include sodium hydride, potassium-tert-butoxide, lithium diisopropylamide, sodium bis (trimethylsilyl)amide and lithium bis(trimethylsilyl)amide. Sodium bis(trimethylsilyl)amide is preferred. Aldol condensations are described in "Modern Synthetic Reactions," Herbert O. House, 2d. Edition, W. A. Benjamin, Menlo Park, Calif., 629–682 (1972) and Tetrahedron, 38 (20), 3059 (1982).

The compounds of formula VI which are basic in nature are capable of forming a wide variety of different salts with various inorganic and organic acids. Although such salts must be pharmaceutically acceptable for administration to animals, it is often desirable in practice to initially isolate a compound of formula VI from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of formula VI are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The compounds of formula VI and their pharmaceutically acceptable salts (hereinafter also referred to as "the active compound") are useful psychotherapeutics and are potent agonists and/or antagonists of the serotonin 1A ($5\text{-}HT_{1A}$) and/or serotonin 1D ($5\text{-}HT_{1D}$) receptors. The active compound is useful in the treatment of hypertension, depression, generalized anxiety disorder, phobias (e.g., agoraphobia, social phobia and simple phobias), posttraumatic stress syndrome, avoidant personality disorder, sexual dysfunction (e.g., premature ejaculation), eating disorders (e.g., anorexia nervosa and bulimia nervosa), obesity, chemical dependencies (e.g., addictions to alcohol, cocaine, heroin, phenolbarbitol, nicotine and benzodiazepines), cluster headache, migraine, pain, Alzheimer's disease, obsessive-compulsive disorder, panic disorder, memory disorders (e.g., dementia, amnestic disorders, and age-related cognitive decline (ARCD)), Parkinson's diseases (e.g., dementia in Parkinson's disease, neuroleptic-induced parkinsonism and tardive dyskinesias), endocrine disorders (e.g., hyperprolactinaemia), vasospasm (particularly in the cerebral vasculature), cerebellar ataxia, gastrointestinal tract disorders (involving changes in motility and secretion), negative symptoms of schizophrenia, premenstrual syndrome, Fibromyalgia Syndrome, stress incontinence, Tourette syndrome, trichotillomania, kleptomania, male impotence, cancer (e.g. small cell lung carcinoma), chronic paroxysmal hemicrania and headache (associated with vascular disorders).

The affinities of the compounds of formula VI for the various serotonin-1 receptors can be determined using standard radioligand binding assays as described in the literature. The 5-$HT_{1A}$ affinity can be measured using the procedure of Hoyer et al. (*Brain Res.*, 376, 85 (1986)). The 5-$HT_{1D}$ affinity can be measured using the procedure of Heuring and Peroutka (*J. Neurosci.*, 7, 894 (1987)).

The in vitro activity of the compounds of formula VI at the 5-$HT_{1D}$ binding site may be determined according to the following procedure. Bovine caudate tissue is homogenized and suspended in 20 volumes of a buffer containing 50 mM TRIS.hydrochloride (tris[hydroxymethyl]aminomethane hydrochloride) at a pH of 7.7. The homogenate is then centrifuged at 45,000 G for 10 minutes. The supernatant is then discarded and the resulting pellet resuspended in approximately 20 volumes of 50 mM TRIS.hydrochloride buffer at pH 7.7. This suspension is then pre-incubated for 15 minutes at 37° C., after which the suspension is centrifuged again at 45,000 G for 10 minutes and the supernatant discarded. The resulting pellet (approximately 1 gram) is resuspended in 150 ml of a buffer of 15 mM TRIS.hydrochloride containing 0.01 percent ascorbic acid with a final pH of 7.7 and also containing 10 $\mu$M pargyline and 4 mM calcium chloride ($CaCl_2$). The suspension is kept on ice at least 30 minutes prior to use.

The inhibitor, control or vehicle is then incubated according to the following procedure. To 50 $\mu$l of a 20 percent dimethylsulfoxide (DMSO)/80 percent distilled water solution is added 200 $\mu$l of tritiated 5-hydroxytryptamine (2 nM) in a buffer of 50 mM TRIS.hydrochloride containing 0.01 percent ascorbic acid at pH 7.7 and also containing 10 $\mu$M pargyline and 4 $\mu$M calcium chloride, plus 100 nM of 8-hydroxy-DPAT (dipropylaminotetraline) and 100 nM of mesulergine. To this mixture is added 750 $\mu$l of bovine caudate tissue, and the resulting suspension is vortexed to ensure a homogenous suspension. The suspension is then incubated in a shaking water bath for 30 minutes at 25° C. After incubation is complete, the suspension is filtered using glass fiber filters (e.g., Whatman GFB-filters™). The pellet is then washed three times with 4 ml of a buffer of 50 mM TRIS.hydrochloride at pH 7.7. The pellet is then placed in a scintillation vial with 5 ml of scintillation fluid (aquasol 2™) and allowed to sit overnight. The percent inhibition can be calculated for each dose of the compound. An $IC_{50}$ value can then be calculated from the percent inhibition values.

The activity of compounds of formula VI for 5-$HT_{1A}$ binding ability can be determined according to the following procedure Rat brain cortex tissue is homogenized and divided into samples of 1 gram lots and diluted with 10 volumes of 0.32 M sucrose solution. The suspension is then centrifuged at 900 G for 10 minutes and the supernate separated and recentrifuged at 70,000 G for 15 minutes. The supernate is discarded and the pellet resuspended in 10 volumes of 15 mM TRIS.hydrochloride at pH 7.5. The suspension is allowed to incubate for 15 minutes at 37° C. After pre-incubation is complete, the suspension is centrifuged at 70,000 G for 15 minutes and the supernate discarded. The resulting tissue pellet is resuspended in a buffer of 50 mM TRIS.hydrochloride at pH 7.7 containing 4 mM of calcium chloride and 0.01 percent ascorbic acid. The tissue is stored at −70° C. until ready for an experiment. The tissue can be thawed immediately prior to use, diluted with 10 $\mu$m pargyline and kept on ice.

The tissue is then incubated according to the following procedure. Fifty microliters of control, inhibitor, or vehicle (1 percent DMSO final concentration) is prepared at various dosages. To this solution is added 200 $\mu$l of tritiated DPAT at a concentration of 1.5 nM in a buffer of 50 mM TRIS.hydrochloride at pH 7.7 containing 4 mM calcium chloride, 0.01 percent ascorbic acid and pargyline. To this solution is then added 750 $\mu$l of tissue and the resulting suspension is vortexed to ensure homogeneity. The suspension is then incubated in a shaking water bath for 30 minutes at 37° C. The solution is then filtered, washed twice with 4 ml of 10 mM TRIS.hydrochloride at pH 7.5 containing 154 mM of sodium chloride. The percent inhibition is calculated for each dose of the compound, control or vehicle. $IC_{50}$ values are calculated from the percent inhibition values.

The agonist and antagonist activities of compounds of formula VI at 5-$HT_{1A}$ and 5-$HT_{1D}$ receptors can be determined using a single saturating concentration according to the following procedure. Male Hartley guinea pigs are decapitated and 5-$HT_{1A}$ receptors are dissected out of the hippocampus, while 5-$HT_{1D}$ receptors are obtained by slicing at 350 mM on a Mcllwain tissue chopper and dissecting out the substantia nigra from the appropriate slices. The individual tissues are homogenized in 5 mM HEPES buffer containing 1 mM EGTA (pH 7.5) using a hand-held glass-Teflon® homogenizer and centrifuged at 35,000×g for 10 minutes at 4° C. The pellets are resuspended in 100 mM HEPES buffer containing 1 mM EGTA (pH 7.5) to a final protein concentration of 20 mg (hippocampus) or 5 mg (substantia nigra) of protein per tube. The following agents are added so that the reaction mix in each tube contained 2.0 mM $MgCl_2$, 0.5 mM ATP, 1.0 mM cAMP, 0.5 mM IBMX, 10 mM phosphocreatine, 0.31 mg/mL creatine phosphokinase, 100 $\mu$M GTP and 0.5–1 microcuries of [$^{32}$P]-ATP (30 Ci/mmol: NEG-003—New England Nuclear). Incubation is initiated by the addition of tissue to siliconized microfuge tubes (in triplicate) at 30° C. for 15 minutes. Each tube receives 20 $\mu$L tissue, 10 $\mu$L drug or buffer (at 10× final concentration), 10 $\mu$L 32 nM agonist or buffer (at 10× final concentration), 20 $\mu$L forskolin (3 $\mu$M final concentration) and 40 $\mu$L of the preceding reaction mix. Incubation is terminated by the addition of 100 $\mu$L 2% SDS, 1.3 mM cAMP, 45 mM ATP solution containing 40,000 dpm [$^3$H]-cAMP (30 Ci/mmol: NET-275—New England Nuclear) to monitor the recovery of cAMP from the columns. The separation of [$^{32}$P]-ATP and [$^{32}$P]-cAMP is accomplished using the method of Salomon et al., *Analytical Biochemistry*, 1974, 58, 541–548. Radioactivity is quantified by liquid scintillation counting. Maximal inhibition is defined by 10 $\mu$M (R)-8-OH-DPAT for 5-$HT_{1A}$ receptors, and 320 nM 5-HT for 5-$HT_{1D}$ receptors. Percent inhibitions by the test compounds are then calculated in relation to the inhibitory effect of (R)-8-OH-DPAT for 5-$HT_{1A}$ receptors or 5-HT for 5-$HT_{1D}$ receptors. The reversal of agonist induced inhibition of forskolin-stimulated adenylate cyclase activity is calculated in relation to the 32 nM agonist effect.

The compounds of formula VI can be tested for in vivo activity for antagonism of 5-$HT_{1D}$ agonist-induced hypothermia in guinea pigs according to the following procedure.

Male Hartley guinea pigs from Charles River, weighing 250–275 grams on arrival and 300–600 grams at testing, serve as subjects in the experiment. The guinea pigs are housed under standard laboratory conditions on a 7 a.m. to 7 p.m. lighting schedule for at least seven days prior to experimentation. Food and water are available ad libitum until the time of testing.

The compounds of formula VI can be administered as solution in a volume of 1 ml/kg. The vehicle used is varied depending on compound solubility. Test compounds are typically administered either sixty minutes orally (p.o.) or 0 minutes subcutaneously (s.c.) prior to a 5-HT$_{1D}$ agonist, such as [3-(1-methylpyrrolidin-2-ylmethyl)-1H-indol-5-yl]-(3-nitropyridin-3-yl)-amine, which can be prepared as described in PCT publication WO 93/11106, published Jun. 10, 1993, which is administered at a dose of 5.6 mg/kg, s.c. Before a first temperature reading is taken, each guinea pig is placed in a clear plastic shoe box containing wood chips and a metal grid floor and allowed to acclimate to the surroundings for 30 minutes. Animals are then returned to the same shoe box after each temperature reading. Prior to each temperature measurement each animal is firmly held with one hand for a 30-second period. A digital thermometer with a small animal probe is used for temperature measurements. The probe is made of semi-flexible nylon with an epoxy tip. The temperature probe is inserted 6 cm into the rectum and held there for 30 seconds or until a stable recording is obtained. Temperatures are then recorded.

In p.o. screening experiments, a "pre-drug" baseline temperature reading is made at −90 minutes, the test compound is given at −60 minutes and an additional −30 minute reading is taken. The 5-HT$_{1D}$ agonist is then administered at 0 minutes and temperatures are taken 30, 60, 120 and 240 minutes later.

In subcutaneous screening experiments, a pre-drug baseline temperature reading is made at −30 minutes. The test compound and 5-HT$_{1D}$ agonists are given concurrently and temperatures are taken at 30, 60, 120 and 240 minutes later.

Data are analyzed with two-way analysis of variants with repeated measures in Newman-Keuls post hoc analysis.

The active compounds of formula VI can be evaluated as anti-migraine agents by testing the extent to which they mimic sumatriptan in contracting the dog isolated saphenous vein strip [P. P. A. Humphrey et al., *Br. J. Pharmacol.*, 94, 1128 (1988)]. This effect can be blocked by methiothepin, a known serotonin antagonist. Sumatriptan is known to be useful in the treatment of migraine and produces a selective increase in carotid vascular resistance in the anesthetized dog. The pharmacological basis of sumatriptan efficacy has been discussed in W. Fenwick et al., *Br. J. Pharmacol.*, 96, 83 (1989).

The serotonin 5-HT$_1$ agonist activity can be determined by the in vitro receptor binding assays, as described for the 5-HT$_{1A}$ receptor using rat cortex as the receptor source and [$^3$H]-8-OH-DPAT as the radioligand [D. Hoyer et al. *Eur. J. Pharm.*, 118, 13 (1985)] and as described for the 5-HT$_{1D}$ receptor using bovine caudate as the receptor source and [$^3$H]serotonin as the radioligand [R. E. Heuring and S. J. Peroutka, *J. Neuroscience*, 7, 894 (1987)].

The compounds of formula VI may advantageously be used in conjunction with one or more other therapeutic agents, for instance, different antidepressant agents such as tricyclic antidepressants (e.g., amitriptyline, dothiepin, doxepin, trimipramine, butripyline, clomipramine, desipramine, imipramine, iprindole, lofepramine, nortriptyline or protriptyline), monoamine oxidase inhibitors (e.g., isocarboxazid, pheneizine or tranylcyclopramine) or 5-HT re-uptake inhibitors (e.g., fluvoxamine, sertraline, fluoxetine or paroxetine), and/or with antiparkinsonian agents such as dopaminergic antiparkinsonian agents (e.g., levodopa, preferably in combination with a peripheral decarboxylase inhibitor e.g., benserazide or carbidopa, or with a dopamine agonist e.g., bromocriptine, lysuride or pergolide).

The compounds of formula VI and the pharmaceutically acceptable salts thereof, in combination with a 5-HT re-uptake inhibitor (e.g., fluvoxamine, sertraline, fluoxetine or paroxetine), preferably sertraline, or a pharmaceutically acceptable salt or polymorph thereof (the combination of a compound of formula VI with a 5-HT re-uptake inhibitor is referred to herein as "the active combination"), are useful psychotherapeutics and may be used in the treatment or prevention of disorders the treatment or prevention of which is facilitated by enhanced serotonergic neurotransmission (e.g., hypertension, depression, generalized anxiety disorder, phobias, posttraumatic stress syndrome, avoidant personality disorder, sexual dysfunction, eating disorders, obesity, chemical dependencies, cluster headache, migraine, pain, Alzheimer's disease, obsessive-compulsive disorder, panic disorder, memory disorders (e.g., dementia, amnestic disorders, and age-associated memory impairment), Parkinson's diseases (e.g., dementia in Parkinson's disease, neuroleptic-induced Parkinsonism and tardive dyskinesias), endocrine disorders (e.g., hyperprolactinaemia), vasospasm (particularly in the cerebral vasculature), cerebellar ataxia, gastrointestinal tract disorders (involving changes in motility and secretion) chronic paroxysmal hemicrania and headache (associated with vascular disorders).

Serotonin (5-HT) re-uptake inhibitors, preferably sertraline, exhibit positive activity against depression; chemical dependencies; anxiety disorders including panic disorder, generalized anxiety disorder, agoraphobia, simple phobias, social phobia, and post-traumatic stress disorder; obsessive-compulsive disorder; avoidant personality disorder and premature ejaculation in mammals, including humans, due in part to their ability to block the synaptosomal uptake of serotonin.

U.S. Pat. No. 4,536,518 describes the synthesis, pharmaceutical composition and use of sertraline for depression and is hereby incorporated by reference in its entirety. PCT publication WO 98/14433 relates to novel aralkyl and aralkylidene heterocyclic lactams and imides, to intermediates for their preparation, to pharmaceutical compositions containing them and to their medicinal use and is hereby incorporated by reference in its entirety.

Activity of the active combination as antidepressants and related pharmacological properties can be determined by methods (1)–(4) below, which are described in Koe, B. et al., *Journal of Pharmacology and Experimental Therapeutics*, 226 (3), 686–700 (1983). Specifically, activity can be determined by studying (1) their ability to affect the efforts of mice to escape from a swim-tank (Porsolt mouse "behavior despair" test), (2) their ability to potentiate 5-hydroxytryptophan-induced behavioral symptoms in mice in vivo, (3) their ability to antagonize the serotonin-depleting activity of p-chloroamphetamine hydrochloride in rat brain in vivo, and (4) their ability to block the uptake of serotonin, norepinephrine and dopamine by synaptosomal rat brain cells in vitro. The ability of the active combination to counteract reserpine hypothermia in mice in vivo can be determined according to the methods described in U.S. Pat. No. 4,029,731.

The compositions of the compounds of formula VI may be formulated in a conventional manner using one or more pharmaceutically acceptable carriers. Thus, the active compounds of formula VI may be formulated for oral, buccal, intranasal, parenteral (e.g., intravenous, intramuscular or subcutaneous) or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcytalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration, the composition may take the form of tablets or lozenges formulated in conventional manner.

The active compounds of formula VI may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g., sterile pyrogen-free water, before use.

The active compounds of formula VI may also be formulated in rectal compositions such as suppositories or retention enemas, e.g., containing conventional suppository bases such as cocoa butter or other glycerides.

For intranasal administration or administration by inhalation, the active compounds of formula VI are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of formula VI and a suitable powder base such as lactose or starch.

A proposed dose of the active compound of formula VI for oral, parenteral or buccal administration to the average adult human for the treatment of the conditions referred to above (e.g., depression) is 0.1 to 200 mg of the active ingredient per unit dose which could be administered, for example, 1 to 4 times per day.

Aerosol formulations for treatment of the conditions referred to above (e.g., migraine) in the average adult human are preferably arranged so that each metered dose or "puff" of aerosol contains 20 μg to 1000 μg of the compound of formula VI. The overall daily dose with an aerosol will be within the range 100 μg to 10 mg. Administration may be several times daily, for example 2, 3, 4 or 8 times, giving for example, 1, 2 or 3 doses each time.

In connection with the use of an active compound of formula VI with a 5-HT re-uptake inhibitor, preferably sertraline, for the treatment of subjects possessing any of the above conditions, it is to be noted that these compounds may be administered either alone or in combination with pharmaceutically acceptable carriers by either of the routes previously indicated, and that such administration can be carried out in both single and multiple dosages. More particularly, the active combination can be administered in a wide variety of different dosage forms, i.e., they may be combined with various pharmaceutically-acceptable inert carriers in the form of tablets, capsules, lozenges, troches, hard candies, powders, sprays, aqueous suspension, injectable solutions, elixirs, syrups, and the like. Such carriers include solid diluents or fillers, sterile aqueous media and various non-toxic organic solvents, etc. Moreover, such oral pharmaceutical formulations can be suitably sweetened and/or flavored by means of various agents of the type commonly employed for such purposes. In general, the compounds of formula I are present in such dosage forms at concentration levels ranging from about 0.5% to about 90% by weight of the total composition, i.e., in amounts which are sufficient to provide the desired unit dosage and a 5-HT re-uptake inhibitor, preferably sertraline, is present in such dosage forms at concentration levels ranging from about 0.5% to about 90% by weight of the total composition, i.e., in amounts which are sufficient to provide the desired unit dosage.

A proposed daily dose of an active compound of formula VI in the combination formulation (a formulation containing an active compound of formula VI and a 5-HT re-uptake inhibitor) for oral, parenteral, rectal or buccal administration to the average adult human for the treatment of the conditions referred to above is from about 0.01 mg to about 2000 mg, preferably from about 0.1 mg to about 200 mg of the active ingredient of formula I per unit dose which could be administered, for example, 1 to 4 times per day.

A proposed daily dose of a 5-HT re-uptake inhibitor, preferably sertraline, in the combination formulation for oral, parenteral or buccal administration to the average adult human for the treatment of the conditions referred to above is from about 0.1 mg to about 2000 mg, preferably from about 1 mg to about 200 mg of the 5-HT re-uptake inhibitor per unit dose which could be administered, for example, 1 to 4 times per day.

A preferred dose ratio of sertraline to an active compound of formula VI in the combination formulation for oral, parenteral or buccal administration to the average adult human for the treatment of the conditions referred to above is from about 0.00005 to about 20,000, preferably from about 0,25 to about 2,000.

Aerosol combination formulations for treatment of the conditions referred to above in the average adult human are preferably arranged so that each metered dose or "puff" of aerosol contains from about 0.01 μg to about 100 mg of the active compound of formula VI, preferably from about 1 μg to about 10 mg of such compound. Administration may be several times daily, for example 2, 3, 4 or 8 times, giving for example, 1, 2 or 3 doses each time.

Aerosol formulations for treatment of the conditions referred to above in the average adult human are preferably arranged so that each metered dose or "puff" of aerosol contains from about 0.01 mg to about 2000 mg of a 5-HT re-uptake inhibitor, preferably sertraline, preferably from about 1 mg to about 200 mg of sertraline. Administration may be several times daily, for example 2, 3, 4 or 8 times, giving for example, 1, 2 or 3 doses each time.

As previously indicated, a 5-HT reuptake inhibitor, preferably sertraline, in combination with compounds of formula VI are readily adapted to therapeutic use as antidepressant agents. In general, these antidepressant compositions containing a 5-HT re-uptake inhibitor, preferably sertraline, and a compound of formula VI are normally administered in dosages ranging from about 0.01 mg to about 100 mg per kg of body weight per day of a 5-HT re-uptake inhibitor, preferably sertraline, preferably from about 0.1 mg to about 10 mg per kg of body weight per day of sertraline; with from about 0.001 mg to about 100 mg per kg of body weight per day of a compound of formula VI, preferably from about 0.01 mg to about 10 mg per kg of body weight per day of a compound of formula VI, although variations will necessarily occur depending upon the conditions of the subject being treated and the particular route of administration chosen.

The following Examples illustrate the preparation of the compounds of the present invention. Melting points are uncorrected. NMR data are reported in parts per million (δ) and are referenced to the deuterium lock signal from the sample solvent (deuteriochloroform unless otherwise specified). Commercial reagents were utilized without further purification.

Preparation A 2-(3,4-Dichloro-phenylamino)-ethanethiol hydrochloride

A 3-necked 2 L round bottomed flask equipped with an overhead stirrer, temperature probe and reflux condenser with Dean-Stark trap was charged with 100.0 grams (0.617 mol) of 3,4-dichloroaniline and 500 mL of toluene. The resulting solution was then treated with 64.4 mL (0.927 mol, 1.5 equivalents) of mercaptoacetic acid. The solution was heated to reflux (130° C.), while collecting water in the Dean-Stark trap for 20 hours, then cooled to room temperature. Ethyl acetate (250 mL) was then added followed by 123 mL of 1N hydrochloric acid. The layers were separated and the organic layer washed with 250 mL of water then 500 mL of saturated aqueous sodium bicarbonate and concentrated under vacuum to a volume of approximately 200 mL. After addition of 200 mL of toluene, the solution was again concentrated to approximately 200 mL, diluted with 1 L of tetrahydrofuran and filtered. This filtrate was added dropwise to a nitrogen-purged 3-necked 5 L round bottomed flask containing 1.73 L (1.73 mol, 2.80 equivalents) of 1N borane-tetrahydrofuran complex while maintaining a temperature of 10–15° C. Some gassing was observed. The reaction mixture was warmed to room temperature and stirred overnight then cooled to 10° C. A solution of 252 grams (6.91 mol, 11.2 equivalents) of anhydrous hydrogen chloride in 840 mL of ethanol was added at 10–15° C. during which time significant gas evolution was observed and solids precipitated. After stirring for 1 hour at 5–10° C. the solids were collected by filtration, washed with tetrahydrofuran, and dried under vacuum to yield 100.0 grams (62.6% yield) of the title compound as a white solid, mp 185–188° C. $^{1}$H NMR (DMF-d$_{7}$) δ7.20 (d, J=8.7 Hz, 1H), 7.01 (d, J=2.7 Hz, 1H), 6.78 (dd, J=2.7, 8.7 Hz, 1H), 3.18 (dd, J=6.4, 7.7 Hz, 2H) 2.61 (br s, 2H), 2.37 (br s, 1H). $^{13}$C NMR (DMF-d$_{7}$) δ146.02, 132.94, 134.90, 122.70, 118.09, 117.19, 50.05, 23.07. HRMS (FAB) calcd for C$_{8}$H$_{9}$Cl$_{2}$NS: 221.9911; found: 221.9893.

EXAMPLE 1

4-(3,4-Dichloro-phenyl)-thiomorpholin-3-one

A 3-necked 3 L round bottomed flask equipped with overhead stirrer, temperature probe, and nitrogen inlet was charged with 100 grams (0.387 mol) of 2-(3,4-dichlorophenylamino)-ethanethiol hydrochloride and 1 L of 2B-ethanol. To the resulting suspension was charged 76 grams (1.35 mol, 3.5 equivalents) of potassium hydroxide. The addition resulted in a temperature increase to approximately 35° C. This suspension was stirred at room temperature for 15–20 minutes, then cooled to 5–10° C. and treated with a solution of 59.1 grams (0.425 mol, 1.1 equivalents) of bromoacetic acid in 152 mL of 2B-ethanol. After stirring at room temperature for approximately 3 hours, the reaction mixture was concentrated under vacuum to a volume of approximately 225 mL. To this suspension was added 864 mL (9.15 mol, 23.6 equivalents) of acetic anhydride with no external cooling which resulted in a temperature increase to approximately 100° C. The flask was fitted with a condenser and receiving flask, and heated to 105–110° C. at which point distillate began to be collected. With continued heating, the internal temperature rose to 115° C., the reaction flask was refitted with a reflux condenser and the reaction mixture held at reflux for 1 hour. After allowing to cool to room temperature, the reaction mixture was poured into a 3-necked 5 L round bottomed flask containing 1700 mL of water and 864 mL of methylene chloride and stirred for 10–20 minutes at 20–25° C. The layers were separated and the organic layer was washed with 1 L of water then treated with 2 L of 10% aqueous sodium hydroxide which brought the pH to 9–10. The layers were separated, the organic layer was dried over magnesium sulfate, and concentrated atmospherically to a volume of approximately 200 mL. Displacement of the methylene chloride by isopropyl ether was accomplished by continuing to charge isopropyl ether and concentrating until an internal temperature of 68° C. was attained. The solution was then cooled to room temperature. Solids began to precipitate at 45° C. The resulting slurry was stirred at room temperature for two hours. The solids were collected by filtration, washed with isopropyl ether and vacuum dried at 45–50° C. to yield 57.5 grams (56.7% yield) of the title compound as a white solid, mp 81–83° C. $^{1}$H NMR (CDCl$_{3}$) δ7.44 (d, J=8.7 Hz, 1H), 7.38 (d, J=2.5 Hz, 1H), 7.13 (d, J=2.5 Hz, 1H), 3.93 (t, J=11.5 Hz, 2H), 3.43 (s, 2H), 3.01 (t, J=11.5 Hz, 2H). $^{13}$C NMR (CDCl$_{3}$) δ168.10, 143.04, 134.201, 132.25, 132.09, 129.42, 126.83, 53.32, 31.81, 27.86. HRMS (FAB) calcd for C$_{10}$H$_{9}$Cl$_{2}$NOS: 261.9860; found: 261.9839.

What is claimed is:

1. A process for preparing a compound of the formula

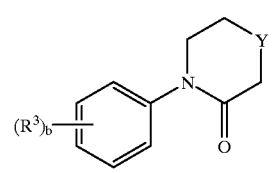

I wherein b is 0, 1, 2 or 3; Y is oxygen, sulfur, NH or N-acetyl; and each R$^{3}$ is independently selected from the group consisting of halo, cyano, (C$_{1}$–C$_{6}$)alkyl, (C$_{1}$–C$_{6}$)alkoxy and trifluoromethyl; comprising reacting a compound of the formula

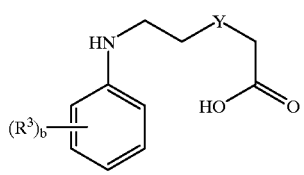

with a dehydrating agent.

2. A process according to claim 1, wherein the dehydrating agent is acetic anhydride.

3. A process according to claim 1, further including preparing the compound of the formula

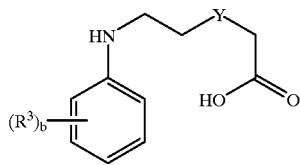

comprising reacting a compound of the formula

with haloacetic acid in the presence of a base.

4. A process according to claim 3, wherein the haloacetic acid is bromoacetic acid.

5. A process according to claim 3, wherein the base is potassium hydroxide.

6. A process according to claim 3, further including preparing the compound of the formula

comprising reacting a compound of the formula

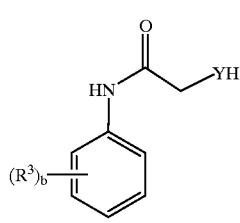

with a reducing agent and reacting the compound so formed with hydrochloric acid.

7. A process according to claim 6, wherein the reducing agent is borane tetrahydrofuran complex.

8. A process according to claim 6, further including preparing the compound of the formula

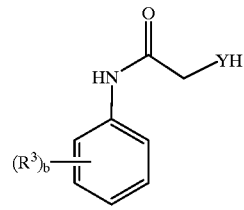

comprising reacting a compound of the formula

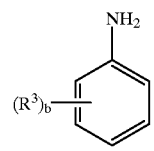

with hydroxyacetic acid, mercaptoacetic acid or 2-aminoacetic acid.

9. A process according to claim 6, wherein the compound of formula V is reacted with mercaptoacetic acid.

10. A process for preparing a compound of the formula

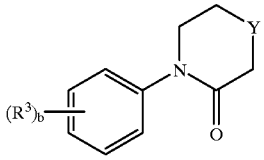

wherein b is 0, 1, 2 or 3; Y is oxygen, sulfur, NH or N-acetyl; and each $R^3$ is independently selected from the group consisting of halo, cyano, $(C_1-C_6)$alkyl, $(C_1-C_6)$alkoxy and trifluoromethyl; comprising (a) reacting a compound of the formula

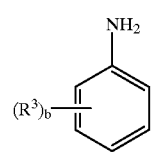

with hydroxyacetic acid, mercaptoacetic acid or 2-aminoacetic acid;

(b) reacting a compound of formula IV so formed

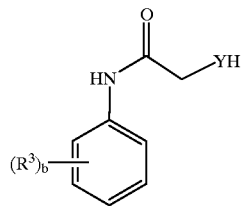

IV with a reducing agent and reacting the compound so formed with hydrochloric acid;
(c) reacting a compound of formula III so formed

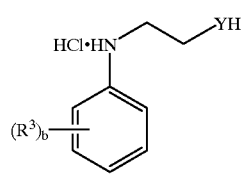

III with haloacetic acid in the presence of a base; and
(d) reacting a compound of formula II so formed

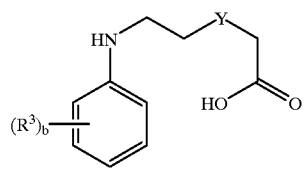

II with a dehydrating agent.

11. A process according to claim 10, wherein the compound of formula V is reacted with mercaptoacetic acid; the reducing agent is borane tetrahydrofuran complex; the base is potassium hydroxide; the haloacetic acid is bromoacetic acid; and the dehydrating agent is acetic anhydride.

12. A compound of the formula

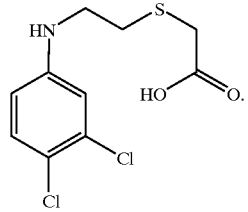

X

13. A compound of the formula

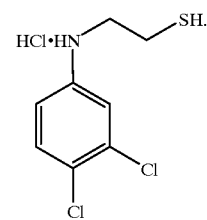

XI

14. A compound of the formula

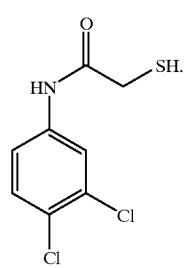

XII

\* \* \* \* \*